United States Patent [19]

Arsura et al.

[11] Patent Number: 4,656,032

[45] Date of Patent: Apr. 7, 1987

[54] **SEXUAL ATTRACTING MIXTURES FOR *COSSUS COSSUS* (LEPIDOPTERA)**

[75] Inventors: Emilio Arsura; Amedeo Capizzi; Giorgio Cassani; Pia Spinelli, all of Milan; Cristina Tonini, Novara, all of Italy

[73] Assignee: Montedison S.p.A., Milan, Italy

[21] Appl. No.: 333,924

[22] Filed: Dec. 23, 1981

[30] Foreign Application Priority Data

Dec. 30, 1980 [IT] Italy .................... 26993 A/80

[51] Int. Cl.$^4$ ........................... A01N 25/00
[52] U.S. Cl. ........................... 424/84
[58] Field of Search ........................... 424/84

[56] References Cited

U.S. PATENT DOCUMENTS

| | | | |
|---|---|---|---|
| 3,560,613 | 2/1971 | Miskus et al. | 424/174 |
| 3,791,983 | 2/1974 | Maierson | 424/84 |
| 3,961,051 | 6/1976 | Emodi | 424/174 |
| 4,042,681 | 8/1977 | Underhill et al. | 424/84 |
| 4,075,783 | 2/1978 | Burden et al. | 424/84 |
| 4,107,293 | 8/1978 | Swailes et al. | 424/84 |
| 4,160,335 | 7/1979 | Von Kohorn et al. | 424/84 |
| 4,301,043 | 11/1981 | Sato et al. | 424/84 |
| 4,323,556 | 4/1982 | Dal Moro et al. | 424/84 |
| 4,325,941 | 4/1982 | Dal Moro et al. | 424/84 |

FOREIGN PATENT DOCUMENTS 2064323  6/1981  United Kingdom .................. 424/84

OTHER PUBLICATIONS

Ando et al. (I) "Lepidopterous Sex Attractants", Agr. Biol. Chem., 39(5), 1163–1165, 1975.
Ando et al. (II) "Sex Attractants for Male Lepidoptera", Agric. Biol. Chem., 41(8), 1485–1492, 1977.
Warthen et al. "Insect Sex Attractants, X, 5-Dodecen-1-ol Acetates, Analogs of the Cabbage Looper Sex Attractant", J. Med. Chem., 11(2), 373–374 (1968).
"Advances in Pest Control Research", vol. 8, p. 88, 1968.

*Primary Examiner*—Albert T. Meyers
*Assistant Examiner*—John M. Kilcoyne

[57] ABSTRACT

Mixtures containing (Z)-5-dodecenyl-acetate optionally combined with other compounds are shown to have a high attracting power for the male insects of the species *Cossus cossus*.

Said mixtures may be employed in traps both for a monitoring action on the population density in a certain area and for mass-captures, or they may be employed for permeating the air in a certain zone, thus preventing the insects from mating.

15 Claims, No Drawings

SEXUAL ATTRACTING MIXTURES FOR COSSUS COSSUS (LEPIDOPTERA)

BACKGROUND OF THE INVENTION

*Cossus cossus* is spread almost all over the palearctic region and in North-Africa. It has a biennial or triennial cycle, the period of maximum adult emergence being the months of June and July.

At the larval-stage it attacks almost all the hardwood trees and it digs deep galleries in the trunks and branches, thus jeopardizing also, seriously, the vitality of the infested plants and degrading the commercial value of the wood.

In late years, it has spread particularly in the fruit-bearing plants and in the poplars, causing serious damages.

At present this lepidopterous is fought by using conventional insecticides. However, the particular biology of such insect renders the conventional fight method little effective.

Knowledge of the substances composing the sexual pheromone of an insect, or the determination of a mixture of substances endowed with a sexual attracting effect for a certain species, generally permits new methods of fight against the infestations of that insect species.

As is known, the female of most of Lepidoptera emits a sexual pheromone which attracts the male for coupling. The natural pheromone mixture, which generally consists of more components and is specific for each species, possesses a high volatility and spreads in the air even to a great distance.

When the pheromone mixture contacts particular senseorgans of the males (i.e., the chemoreceptive sensilla prevailingly located on the antennae) it attracts the insect towards the source.

When a mixture of substances having a similar effect is available, it is possible to prepare a trap containing the attracting mixture in a suitable composition capable of ensuring a controlled release thereof. The males of the species, coming into contact with the mixture spread in the air, are attracted towards the trap where they are captured and killed.

Use of the said traps permits mass-captures of males of the species, thereby drastically reducing the number of couplings and, by consequence, of future populations of the insect.

Another useful utilization of the traps containing sexual attractants is that of promoting a monitoring action. In fact, by detecting the number of captures in traps containing an attracting mixture and properly located in a zone probably subject to infestation, it is possible to determine, with sufficient accuracy, the limits of the infested zone and the insect population density in such zone. These data permit intervention whenever and wherever necessary by using conventional insecticides.

The monitoring action permits therefore, reduction of the number of treatments to those which are strictly required and to limit them to the zone where infestations may occur, which results in economic and environmental advantages and adversely affects the development of insect strains resistant to the insecticide utilized.

Another useful utilization of a sexual attracting mixture for insects consists in permeating an infested zone, in the mating period, with the attracting mixture. As a consequence thereof, the males of the species are no longer able to locate the females and the amount of couplings decreases, thus drastically reducing the future insect population in such zone.

As far as we know, no researches have been carried out previously on the adults of *Cossus cossus* with a view to identifying the pheromone or mixtures endowed with an analogous effect.

THE PRESENT INVENTION

We have now found that the compound (Z)-5-dodecen-1-yl-acetate possesses an attracting power for the males of the species *Cossus cossus* and that its action can be enhanced by combining it with one or more of the following compounds: (Z)-3-decen-1-yl-acetate, (Z)-3-dodecen-1-yl-acetate and (E)-5-dodecen-1-yl-acetate.

Thus, it is an object of the present invention to provide sexual attracting mixtures for the males of species *Cossus cossus* containing compound (Z)-5-dodecen-1-yl acetate optionally combined with one or more of the aforesaid compounds, along with liquid vehicles or solid carriers and optionally other additives.

When the mixtures of the present invention contain, besides (Z)-5-dodecenyl-acetate, also one or more of the aforementioned compounds, the latter may be present in the mixtures in a ratio ranging from 1:1 to 1:9 by weight, in respect of (Z)-5-dodecenyl-acetate.

Another object of this invention is to provide a method for attracting the males of species *Cossus cossus* into traps containing the above-cited mixtures, wherein they are then captured or killed.

A further object of this invention is to provide a method for determining the infestation degree of *Cossus cossus* in a certain zone by capturing the males of such species in traps containing the (Z)-5-dodecen-1-yl-acetate of this invention, or the mixtures thereof of this invention.

A still further object of the present invention is to provide a method for disturbing and preventing the mating of the insects belonging to species *Cossus cossus*, which consists in permeating the infested zone with the attractant of this invention or mixtures thereof of this invention.

(Z)-5-dodecenyl-acetate (hereinafter referred to as Z-5-$C_{12}$-Ac) is a compound contained in the pheromone mixture of the females of species *Cossus cossus*. It was possible to determine that through extraction, location and characterization operations effected by employing both females and males of said species.

The insects utilized for such work were obtained from grown-up larvae captured in infested elm trees.

Males and females were separated from each other at the pupae stage and the adults were kept in a climatic chamber with a cycle of 8 hours of darkness and 16 hours of light, at a temperature ranging from 17° to 28° C. and at a relative humidity varying from 90 to 40%. Both the males and the females were utilized 2-3 hours after the beginning of the scoto-stage.

From 2-3 days old virgin females the ovipositors were surgically extirpated, and extracted with distilled hexane.

The extract was directly subjected to gaschromatographic analysis (GLC). The GLC analyses were carried out by means of the following equipment:

WCOT (wall-coated open tubular) glass capillary column, filling OV-101, length: 30 m, inside diameter: 0.21 mm;

Gas-chromatograph Carlo Erba model 4160 with flame ionization detector and control modulus for injections in split-less automatic;

WCOT glass capillary column, filling Carbowax 20 M, length: 50 m, inside diameter: 0.23 mm;

Gas-chromatograph Carlo Erba model 2150 with flame ionization detector.

The GLC analysis of the extract in hexane carried out on OV-101 column revealed several peaks, three of them, in a predominant amount, located in the chromatogram area corresponding, as retention time, to the acetates of alcohols having 12 and 14 carbon atoms.

The GLC analyses of the extract in hexane and of the extract additioned with the suitable compounds, carried out on a Carbowax 20 M column permitted to attribute to two of the main peaks the following structures: dodecyl acetate [$C_{12}$-Ac], (Z)-5-dodecenyl-acetate [Z-5-$C_{12}$-Ac].

The third peak, falling within the area of the acetates of alcohols having 14 carbon atoms, was identified as (Z)-5-tetradecenyl-acetate [Z-5-$C_{14}$-Ac].

The attributions of the peaks were confirmed by mass spectroscopy associated with gas-chromatography (GLC-MS). The GLC-MS analysis was carried out with a chromatograph Varian 1400 interfaced with a mass spectrometer Varian-MAT 112 S.

An electroantennography (EAG) was then carried out by isolating the antennae of the 2–3 days old males of *Cossus cossus*. The EAG results proved the reaction of the antenna to compounds $C_{12}$-Ac and Z-5-$C_{12}$-Ac, with a preference for the latter.

To carry out the EAG, the antennae were put in a "bridge"-like position between two beakers containing Kaissling solution [Journal Insect Physiol. 22, 1357 (1975)] and the response signal was picked up by two Ag/AgCl electrodes connected with an amplified differential oscillograph Tektronic 5103 N.

Pasteur pipettes were then prepared, which contained 1 μg of the compounds to be tested in a distilled n-hexane solution. The solvent was allowed to evaporate for about 15 minutes.

The compounds wer then tested by means of a 3 ml "puff" of air flowing through the Pasteur pipettes and injected into a glass tube, through which flowed, continuously, a humidified air stream (0.5 l/min.), and was then positioned at about 2 cm from the antenna.

Field tests were then carried out for capturing the males of species *Cossus cossus* by means of traps charged with different compounds and mixtures thereof in proper compositions. The operative modalities are described in Example 1, infra.

The results of the field tests evidenced the following:

(a) Z-5-$C_{12}$-Ac, which is a component of the natural pheromone mixture, possesses also alone a certain attracting power.

(b) Compounds (Z)-3-decen-1-yl-acetate (Z-3-$C_{10}$-Ac), (Z)-3-dodecen-1-yl-acetate (Z-3-$C_{12}$-Ac) and (E)-5-dodecen-1-yl-acetate (E-5-$C_{12}$-Ac), which were not detected in the natural pheromone mixture within the instrumental limits, do not possess any attracting power.

(c) The mixtures consisting of Z-5-$C_{12}$-Ac and one or more compounds selected from among Z-3-$C_{10}$-Ac, Z-3-$C_{12}$-Ac and E-5-$C_{12}$-Ac have a higher attracting power than that of Z-5-$C_{12}$-Ac alone.

Since it is known that the natural pheromone mixture of an insect is generally composed of more than one compound and that the attracting power of the mixture is strictly connected with the presence of all the components in very exact ratios, (see for example, for a general treatment, W. L. Roelof, R. T. Carde, Ann. Rev. Entomol. 22 377–405 (1977)), and since in the natural pheromone mixture of *Cossus cossus* there was detected the presence of several compounds, it is surprising that Z-5-$C_{12}$-Ac alone possesses attracting power, and it is even more surprising that the attracting power of Z-5-$C_{12}$-Ac may be increased through the combination with other compounds not contained in the natural pheromone mixture.

The attracting power of the mixtures of the present invention for the males of species *Cossus cossus* is sufficiently high as to permit the use thereof in the fight against this insect both through mass-captures of males in suitably prepared traps, and by disturbing the mating by distributing, in the infested area, the properly formulated attracting mixture.

In consequence, it is possible also to employ traps containing the aforesaid mixtures for a monitoring action in order to detect the infestation area and degree.

The traps for insects generally consist of rigid supports which are bent in such manner as to form an inner recess communicating with the outside. The inner side of the rigid supports is coated with an adhesive capable of retaining the insect alighting thereon.

As an alternative, the traps may be equipped with mechanical devices which prevent the insect from leaving the trap, or with insecticides which kill the insect when it enters the trap, either or not combined with the previously mentioned capture methods.

The attracting (Z)-5-$C_{12}$-Ac or mixture may be used in the trap as such or it may be dissolved in suitable inert solvents, such as hydrocarbons, or emulsified in water or, preferably, absorbed on solid carriers, such as, for example, paper, cloth, clay, sawdust, rubber, polymeric materials, etc. Other additives, such as antioxidants, U.V. stabilizers, etc., may be added to the mixtures.

Particularly suitable for such purposes are the distributing devices made of rubber, which may be optionally treated with antioxidizing substances capable of protecting the attracting (Z)-5-$C_{12}$-Ac or mixture from environmental oxidizing action.

Also commercially available are some types of traps suited to the purpose, already equipped with rubber distributing devices and with adhesive, such as, for example, the "Traptest" traps (registered trademark of Montedison S.p.A.).

Since the adult male of species *Cossus cossus* has considerable dimensions (70–90 mm of wing span), should it be required to effect mass-captures, it would be necessary to use traps having a proper geometry and proper characteristics, such as for example those described by Teich and Neumark in "Odour Communication in Animals" (F. J. Ritter Ed.) Elsevier North Holland Biomedical Press, page 343 (1979), or the water traps described by Neumark and coll. in Environmental Letters 10, 97 (1975).

The number of traps and their location in the concerned area mainly depends on the purpose for which they are used (mass-captures or monitoring action).

When the attractant is to be employed for permeating an infested area in order to disturb and prevent the mating, it is necessary to properly formulate it so as to get an adequately slow, constant and uniform release thereof in the air.

For this purpose, it is useful to prepare compositions consisting of the attractant, a liquid vehicle or a solid carrier and optionally other additives, such as antioxidants, U.V. stabilizers, etc.

Suitable liquid vehicles include oils and greases and, more generally, solvents with low vapor tension. Suitable solid supports or carriers are rubber, powdered carbon, sawdust, silicates, pumice, clay, celite, cork and, in general, substances capable of releasing the attractant to the environment in a slow and constant manner.

Another useful method of slow and controlled release which has been employed with the natural pheromones and is employable with the attractants of this invention consists in filling hollow fibers or capillaries closed at one end with the attractant, so that the attractant may be slowly released to the environment from the open end.

It is also possible to prepare microcapsules filled with the attractant, according to known techniques.

Furthermore, the solid compositions may be coated with a thin polymeric film through which the $Z$-5-$C_{12}$-Ac or mixture can slowly spread.

The amount of attractant to be employed varies in relation to the fighting procedure to be followed.

In the traps, either destined to mass-captures or to a monitoring action, the amount of attracting mixture to be used is low in order not to saturate the environment and to permit the male of the species to detect the trap to be reached. In this case the attracting mixture amount is of the order of milligrams or fractions thereof for each trap.

Should it be desired to permeate the environment in order to prevent the insects from mating, the amount of attractant to be employed varies as a function of the type of composition used and of climatic and environmental factors. An amount of the order of a few grams of the attractant per hectare is generally sufficient.

The components of the attracting mixture forming the object of the present invention are generally known compounds or compounds preparable from known precursors. $Z$-5-$C_{12}$-Ac of formula:

is described, along with isomer $E$-5-$C_{12}$-Ac, in J. Med. Chem. 11 (2), 373 (1968) [Chem. Abstr. 68, 95617].

$Z$-3-$C_{12}$-Ac may be prepared, for example, as described in Khim. Sredstva Zashch. Rast. 7, 82 (1976) [Chem. Abstr. 91, 107626 r].

$Z$-3-$C_{10}$-Ac, as far as we know, was not previously described. The preparation thereof is carried out by acetylation, with acetyl chloride, of $Z$-3-decen-1-ol alcohol. Said alcohol has been described in Tetr. Lett. 47, 4231 (1976).

EXAMPLE 1

Capture tests of males of species *Cossus cossus*.

The field tests were conducted near Milan, Italy in an avenue with plane trees and poplars, at S. Cristina (Pavia), close to a mixed wood of alder trees, maples and poplars, and at Nebbiuno (Novara) Italy in a wood of chestnut trees, elm trees and ash trees. The tests were carried out in the period from July 7 to 28, 1980.

There were employed "Traptest" traps treated with adhesive and equipped with rubber distributing devices treated with proper antioxidants, in which the compounds (or the mixtures) to be tested were absorbed. The traps were suitably located (at about 1.5–2 m from the ground) in the zones involved in the test.

The captures were detected every 3–4 days and at each detection a "randomization" of the traps' position was effected, while simultaneously replacing the adhesive-coated bottom.

The following Table shows the results of the tests expressed as average number of captured males for each trap during a week in relation to the attractant employed.

TABLE

Captures of Males of Species *Cossus cossus*

| Test No. | Composition of the attractant (mg)[a] | Average number of captured males per trap per week[b] |
|---|---|---|
| 1 | $Z$—5-$C_{12}$—Ac (1) | 1.7 |
| 2 | $Z$—5-$C_{12}$—Ac (10) | 1.5 |
| 3 | $Z$—3-$C_{10}$—Ac (1) | 0 |
| 4 | $Z$—3-$C_{12}$—Ac (1) | 0 |
| 5 | $E$—5-$C_{12}$—Ac (1) | 0 |
| 6 | $Z$—5-$C_{12}$—Ac (0.5) + $Z$—3-$C_{10}$—Ac (0.5) | 7.8 |
| 7 | $Z$—5-$C_{12}$—Ac (0.8) + $Z$—3-$C_{10}$—Ac (0.2) | 11.6 |
| 8 | $Z$—5-$C_{12}$—Ac (8) + $Z$—3-$C_{10}$—Ac (2) | 17.4 |
| 9 | $Z$—5-$C_{12}$—Ac (0.5) + $Z$—3-$C_{12}$—Ac (0.5) | 5.7 |
| 10 | $Z$—5-$C_{12}$—Ac (0.5) + $E$—5-$C_{12}$—Ac (0.5) | 4.0 |
| 11 | $Z$—5-$C_{12}$—Ac (0.8) + $Z$—3-$C_{10}$—Ac (0.1) + $E$—5-$C_{12}$—Ac (0.1) | 5.9 |

Notes to the table:
[a]$Z$—5-$C_{12}$—Ac = (Z)—5-dodecenyl acetate
$Z$—3-$C_{10}$—Ac = (Z)—3-decenyl acetate
$Z$—3-$C_{12}$—Ac = (Z)—3-dodecenyl acetate
$E$—5-$C_{12}$—Ac = (E)—5-dodecenyl acetate
[b]Average value of at least three tests repeated three times.

From the data recorded in the Table it is apparent that:

(Z)-5-dodecenyl-acetate has a certain attracting power towards the males of species *Cossus cossus* (tests 1 and 2);

other compounds being tested do not show, per se, any attracting power (tests 3–5); the attracting power of

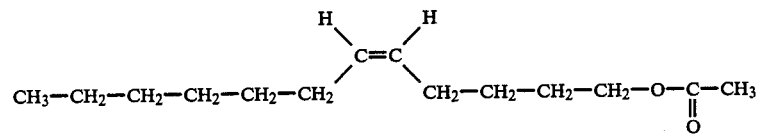

Z-5-C$_{12}$-Ac can be enhanced by about 2–10 times by combining such compound, in the attracting mixture, with other compounds in variable amounts (tests 6–11).

EXAMPLE 2

Preparation of (Z)-3-decen-1-yl acetate

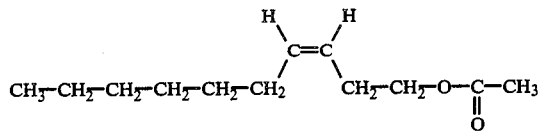

0.011 mols of acetyl chloride were added dropwise, at room temperature, to a solution of 0.01 mols of (Z)-3-decen-1-ol in 20 ml of anhydrous benzene containing 0.011 mols of pyridine.

After a 2-hour stirring at room temperature, the reaction mixture was poured into water and extracted with hexane. The extracts were put together and washed with water, with a sodium chloride-saturated solution and were then anhydrified on anhydrous sodium sulphate.

After removal of the solvents at reduced pressure, the desired product with a yield of 95% was obtained. [IR(cm$^{-1}$) 1700 ($\nu$C=O)].

We claim:

1. An attracting mixture for the males of species *Cossus cossus* containing (a) the compound (Z)-5-dodecen-1-yl-acetate and (b) at least one compound selected from the group consisting of (Z)-3-decen-1-yl acetate, (Z)-3-dodecen-1-yl-acetate and (E)-5-dodecen-1-yl-acetate, the compounds (b) being present in the mixture in a ratio by weight of 1:1 to 1:9 in respect to the (Z)-5-dodecen-1-yl-acetate.

2. A mixture according to claim 1, consisting of (Z)-5-dodecen-1-yl-acetate and (Z)-3-decen-1-yl-acetate.

3. An attracting composition for the males of species *Cossus cossus*, containing an attracting mixture according to claim 1, in a liquid vehicle or on a solid support.

4. An attracting mixture according to claim 1 and also comprising additives selected for antioxidants and U.V. stabilizers.

5. An attracting mixture according to claim 1 and also comprising a liquid vehicle or a solid support and additives selected from antioxidants and U.V. stabilizers.

6. A method of attracting male insects of species *Cossus cossus* into a trap, consisting in employing in the trap an effective amount of the compound (Z)-5-dodecen-1-yl-acetate or of a mixture thereof with at least one compound selected from the group consisting of (Z)-3-decen-1-yl-acetate, (Z)-3-dodecen-1-yl-acetate and (E)-5-dodecen-1-yl-acetate, the last mentioned compounds being present in the mixture in a ratio by weight of 1:1 to 1:9 in respect to the (Z)-5-dodecen-1-yl-acetate, as such or in the form of a composition.

7. A method of attracting male insects of species *Cossus cossus* into a trap, consisting in employing in the trap an effective amount of a mixture comprising (Z)-5-dodecen-1-yl acetate with at least one compound selected from the group consisting of (Z)-3-decen-1-yl-acetate, (Z)-3-dodecen-1-yl-acetate, and (E)-5-dodecen-1-yl-acetate, as such or in the form of a composition also comprising a liquid vehicle or a solid support.

8. The method of claim 7, in which a mixture is employed in the trap and comprises (Z)-3-dodecen-1-yl-acetate in addition to (Z)-5-dodecen-1-yl-acetate.

9. A method of attracting male insects of species *Cossus cossus* into a trap, consisting in employing in the trap an effective amount of a mixture according to claims 1 or 2, as such, or in the form of a composition.

10. A method of fighting infestations of the insect *Cossus cossus*, consisting in attracting the males of said species into traps where they are captured or killed, characterized in that in the traps there is employed, as attractant, an effective amount of (Z)-5-dodecen-1-yl acetate or of a mixture thereof with at least one compound selected from the group consisting of (Z)-3-decen-1-yl-acetate, (Z)-3-dodecen-1-yl-acetate and (E)-5-dodecen-1-yl acetate, the last mentioned compounds being present in the mixture in a ratio by weight of 1:1 to 1:9 in respect to the (Z) 5 dodecen-1-yl-acetate, as such or in the form of a composition.

11. A method of fighting infestations of the insect *Cossus cossus*, consisting in attracting the males of such species into traps where they are captured or killed, characterized in that in the traps there is employed, as attractant, an effective amount of a mixutre according to claim 1, either as such or in the form of a composition also comprising a liquid vehicle or a solid support.

12. A method of detecting the presence of infestations and the density of population of insects of species *Cossus cossus* in a selected zone by capturing the males of such species in traps, characterized in that in the traps there is employed an effective amount of (Z)-5-dodecen-1-yl-acetate or of a mixture thereof with at least one compound selected from the group consisting of (Z)-3-decen-1-yl-acetate, (Z)-3-dodecen-1-yl-acetate and (E)-5-dodecen-1-yl-acetate, the last mentioned compounds being present in the mixture in a ratio by weight of 1:1 to 1:9 in respect to the (Z)-5-dodecen-1-yl-acetate, as such or in the form of a composition.

13. A method of detecting the presence of infestations and the density of population of insect *Cossus cossus* in a selected area by capturing the males of such species in traps, characterized in that in the traps there is employed, as attractant, an effective amount of a mixture according to claims 1 or 2, either as such or in the form of a composition.

14. A method of fighting infestations of insects belonging to species *Cossus cossus* in a selected zone by disturbing and preventing the mating consisting in permeating the air in said zone with an effective amount of (Z)-5-dodecen-1-yl-acetate or of a mixture thereof with at least one cmpound selected from the group consisting of (Z)-3-decen-1-yl-acetate, (Z)-3-dodecen-1-yl-acetate and (E)-5-dodecen-1-yl-acetate, the last mentioned compounds being present in the mixture in a ratio by weight of 1:1 to 1:9 in respect to the (Z)-5-dodecen-1-yl-acetate, in a suitable composition.

15. A method of fighting infestations of insects belonging to species *Cossus cossus* in a selected zone by disturbing and preventing the mating, consisting in permeating the air in said zone with an effective amount of a mixture according to claims 1 or 2, in a suitable composition.

* * * * *